United States Patent
Itoh et al.

[11] Patent Number: 5,387,599
[45] Date of Patent: Feb. 7, 1995

[54] TRIAZOLES, THEIR PRODUCTION AND USE

[75] Inventors: Katsumi Itoh; Kenji Okonogi, both of Osaka, Japan

[73] Assignee: Takeda Chemical Industries, Ltd., Osaka, Japan

[21] Appl. No.: 669,000

[22] Filed: Mar. 13, 1991

[30] Foreign Application Priority Data

Mar. 15, 1990 [JP] Japan .................................. 2-65888

[51] Int. Cl.$^6$ .................. A61K 31/41; C07D 413/12; C07D 403/12; C07D 401/12
[52] U.S. Cl. ...................... 514/383; 514/236.2; 514/252; 514/326; 544/132; 544/366; 546/210; 548/267.6; 548/266.6
[58] Field of Search ...................... 514/383; 548/267.6

[56] References Cited

FOREIGN PATENT DOCUMENTS 0332387 3/1989 European Pat. Off. .

Primary Examiner—Patricia L. Morris
Attorney, Agent, or Firm—Foley & Lardner

[57] ABSTRACT

A triazole compound of the formula (I):

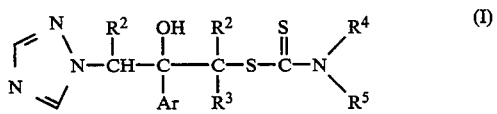

wherein Ar is a substituted phenyl group, $R^1$, $R^2$ and $R^3$ each represents, the same or different, a hydrogen atom or a lower alkyl, $R^4$ and $R^5$ each represents, the same or different, a hydrogen atom, an alkyl group, an aralkyl group, an aryl group or an aromatic heterocyclic group or $R^4$ and $R^5$ together with the nitrogen atom to which they are attached may form a heterocyclic ring, or its salt, which is useful as antifungal agents.

21 Claims, No Drawings

TRIAZOLES, THEIR PRODUCTION AND USE

BACKGROUND OF THE INVENTION

1. Field of the Invention

The present invention relates to novel triazole compounds, their production and use.

2. Description of the Prior Art

Various compounds have so far been disclosed as an antifungal agent.

For example, European Patent Publication No. A-0332387 discloses certain triazole derivatives having fungicidal activity, which however do not possess such moiety of —S—CS—N— in the group to be attached to the triazole moiety.

There is still an eager demand to develop compounds having characteristics of potent fungicidal activity, high tolerance, safety and so forth.

SUMMARY OF THE INVENTION

The present invention provides a triazole compound of the formula (I):

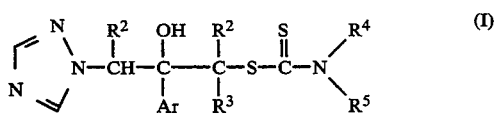

wherein Ar is a substituted phenyl group, $R^1$, $R^2$ and $R^3$ each represents, the same or different, a hydrogen atom or a lower alkyl, $R^4$ and $R^5$ each represents, the same or different, a hydrogen atom, an alkyl group, an aralkyl group, an aryl group or an aromatic heterocyclic group or $R^4$ and $R^5$ together with the nitrogen atom to which they are attached may form a heterocyclic ring, or its salt; a process for preparing the above mentioned compound (I) or its salt and an antifungal agent containing the above-mentioned compound (I) or its salt.

PREFERRED EMBODIMENTS OF THE INVENTION

In the definition of the compound (I), the substituted phenyl group represented by Ar means the phenyl group having one to three substituents selected independently from a halogen and trifluoromethyl, specifically such as 2,4-difluorophenyl, 2,4-dichlorophenyl, 4-fluorophenyl, 4-chlorophenyl, 4-trifluoromethylphenyl, 2-fluoro-4-chlorophenyl, 2-chloro-4-fluorophenyl or 4-bromophenyl, among which 2,4-difluorophenyl is preferable.

Examples of the lower alkyl groups represented by $R^1$, $R^2$ or $R^3$ are a straight or branched chain $C_{1-3}$ alkyl group such as methyl, ethyl, propyl or isopropyl.

$R^2$ and $R^3$ are preferably methyl and hydrogen, respectively.

The alkyl group represented by $R^4$ and $R^5$ includes a straight or branched chain alkyl group having one to twelve carbon atoms, such as methyl, ethyl, propyl, butyl, heptyl, octyl, nonyl, decyl or dodecyl.

The aralkyl group represented by $R^4$ and $R^5$ includes a phenyl($C_{1-4}$) alkyl group such as benzyl, phenethyl, phenylpropyl or the like or a naphthyl($C_{1-4}$) alkyl group such as naphthylmethyl, naphthylethyl or the like.

Examples of the aryl groups represented by $R^4$ and $R^5$ are phenyl, naphthyl, biphenyl, anthryl or indenyl.

Examples of the aromatic heterocyclic groups represented by $R^4$ and $R^5$ are five or six membered heterocyclic groups containing one to four hetero atoms selected from oxygen, sulfur and nitrogen, such as furyl, thienyl, pyridyl, pyrimidinyl, thiazolyl, imidazolyl, triazolyl, pyrazolyl, thiadiazolyl, pyrrolyl, pyrazinyl, isoxazolyl, oxazolyl, tetrazolyl or the like.

Examples of the heterocyclic rings formed by $R^4$ and $R^5$ together with the adjacent nitrogen to which they are attached are five to ten membered heterocyclic rings containing at least one nitrogen and optionally oxygen, such as morpholino, piperidino, piperazinyl, pyrrolidinyl, indolinyl, isoindolinyl, 1,2,3,4-tetrahydroquinolyl, 1,2,3,4-tetrahydroisoquinolyl or the like.

The groups represented by $R^4$ and $R^5$ may have one to three substituents such as a hydroxy group, a carboxyl which may be esterified (e.g., carboxy, ethoxycarbonyl, methoxycarbonyl or butoxycarbonyl), an amino group, an acylamino group (e.g., acetylamino, propionylamino or butyrylamino), an alkylamino group (e.g., methylamino, dimethylamino, diethylamino or dibutylamino), an alkoxy group (e.g., methoxy, ethoxy or butoxy), a halogen (e.g., fluorine, chlorine or bromine), a halogenated alkyl (e.g., trifluoromethyl, dichloromethyl or trifluoroethyl), an oxo group, a thioxo group, a mercapto group, an alkylthio (e.g., methylthio, ethylthio or butylthio), acyl group (e.g., acetyl, formyl, propionyl or butyryl), a heterocyclic group (e.g., pyridyl, furyl or thienyl), an alkyl group (e.g., methyl, ethyl, propyl, butyl or pentyl), a cycloalkyl group (e.g., cyclopropyl, cyclobutyl, cyclopentyl, cyclohexyl or cycloheptyl) or an aryl group (e.g., phenyl or naphthyl).

Examples of the interesting compounds (I) of the present invention are listed in Table 1.

TABLE 1

| Compound No. | Configuration C* | Configuration C** | $\begin{array}{c} R^4 \\ / \\ N \\ \backslash \\ R^5 \end{array}$ |
|---|---|---|---|
| 1 | RS | RS | —N(CH₂CH₃)₂ |
| 2 | R | R | —N(CH₂CH₃)₂ |
| 3 | RS | RS | morpholino |
| 4 | R | R | morpholino |
| 5 | RS | RS | 4-acetylpiperazinyl (—N⟨⟩N—COCH₃) |

TABLE 1-continued

[Structure: triazole-N-CH₂-C*(OH)(2,4-difluorophenyl)-C**H(CH₃)-S-C(=S)-NR⁴R⁵]

| Compound No. | Configuration C* | Configuration C** | NR⁴R⁵ |
|---|---|---|---|
| 6 | R | R | -N(piperazine)N-COCH₃ |
| 7 | RS | RS | -N(piperazine)N-phenyl |
| 8 | R | R | -N(piperazine)N-phenyl |
| 9 | R | R | -N(CH₃)-(3-methylphenyl) |
| 10 | R | R | -N(2,6-dimethylmorpholine) |
| 11 | R | R | -N(piperidine) |
| 12 | R | R | -N(CH₃)-CH₂-(1-naphthyl) |
| 13 | R | R | -N(CH₂CH₂CH₂CH₃)₂ |
| 14 | R | R | -NH-phenyl |
| 15 | R | R | -N(1,2,3,4-tetrahydroquinolinyl) |
| 16 | R | R | -N(indolinyl) |
| 17 | R | R | -NH-(2-COOCH₃-phenyl) |
| 18 | R | R | -NH-(2,3-difluorophenyl) |
| 19 | R | R | -NH-(2,4-difluorophenyl) |
| 20 | R | R | -N((CH₂)₃CH₃)-phenyl |
| 21 | R | R | -NH-(4-CF₃-phenyl) |
| 22 | R | R | -NHCH₂CH₂-phenyl |
| 23 | R | R | -NH-(2,4-dichlorophenyl) |

TABLE 1-continued

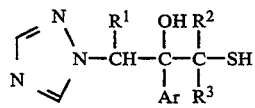

| Compound No. | Configuration C* | Configuration C** | ![N-R⁴/R⁵] |
|---|---|---|---|
| 24 | R | R | −NH−(2,6-dichlorophenyl) |
| 25 | R | R | −NH−(2,6-difluorophenyl) |
| 26 | R | R | −NH−(pyridin-4-yl) |
| 27 | R | R | −NH−(pyridin-2-yl) |
| 28 | R | R | −NH−(thiazol-2-yl) |
| 29 | R | R | −NH−(pyrimidin-2-yl) |
| 30 | R | R | −NH−(1,3,4-thiadiazol-2-yl) |
| 31 | R | R | −N(pyrrolidinyl) |
| 32 | R | R | −N(CH₃)₂ |

The compound (I) of the invention can be prepared by reacting a compound of the formula (II):

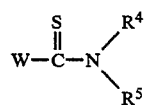

(in which symbols are the same as defined above.) with a compound of the formula (III):

$$W-\overset{S}{\underset{\|}{C}}-N\overset{R^4}{\underset{R^5}{\diagdown}}$$ (III)

(in which $R^4$ and $R^5$ have the same meanings as defined above and W is a halogen atom such as chlorine, bromine or iodine). The reaction can be carried out in water or an organic solvent (e.g., ethyl acetate, methylene chloride, dioxane, diethyl ether, tetrahydrofuran, acetone, benzene, chloroform, dimethylformamide, dimethylsulfoxide, methanol or ethanol) or without any solvent at a temperature in the range of from about −20° C. to about 100° C. The above solvents may be used singly or as a mixture thereof. The reaction can be accelerated by employing, in the reaction system, a base such as triethylamine, pyridine, potassium carbonate, potassium hydroxide, sodium carbonate, sodium hydroxide, sodium methylate or sodium hydrogen carbonate.

The compound (I) of the invention can also be prepared by reacting a compound of the formula (IV):

(in which $R^4$ and $R^5$ have the same meanings as defined above.) with thiophosgen, and thereafter, with the compound of the formula (II). The reaction can be carried out in water or an organic solvent (e.g., ethyl acetate, methylene chloride, dioxane, diethyl ether, tetrahydrofuran, acetone, benzene, chloroform, dimethylformamide, dimethylsulfoxide, methanol or ethanol) or without any solvent at a temperature in the range of from about −20° C. to about 100° C. The above solvents may be used singly or as a mixture thereof. The reaction can be accelerated by employing, in the reaction system, a base such as triethylamine, pyridine, potassium carbonate, potassium hydroxide, sodium carbonate, sodium hydroxide, sodium methylate or sodium hydrogen carbonate.

The compound (I) of the invention can further be prepared by reacting the compound of the formula (II) with thiophosgen, and thereafter, with the compound of the formula (IV). The reaction can be carried out in water or an organic solvent (e.g., ethyl acetate, methylene chloride, dioxane, diethyl ether, tetrahydrofuran, acetone, benzene, chloroform, dimethylformamide, dimethylsulfoxide, methanol or ethanol) or without a solvent at a temperature in the range of from about −20° C. to about 100° C. The above solvents may be used singly or as a mixture thereof. The reaction can be accelerated by employing, in the reaction system, a base such as triethylamine, pyridine, potassium carbonate, potassium hydroxide, sodium carbonate, sodium hydroxide, sodium methylate or sodium hydrogen carbonate.

Moreover, the compound (I) of the present invention in which $R^4$ is a hydrogen atom can be prepared by reacting the compound of the formula (II) with a compound of the formula (V):

$$S=C=N-R^5 \qquad (V)$$

(in which $R^5$ has the same meanings as defined above). The reaction can be carried out in an organic solvent (e.g., chloroform, methylene chloride, dioxane, diethyl ether, tetrahydrofuran, acetone or benzene), or without any solvent at a temperature in the range of from about $-20°$ C. to about $100°$ C. The reaction can be accelerated by employing, in the reaction system, a base such as triethylamine, pyridine, sodium methylate or sodium ethylate.

The compounds (I) of the invention contain one or more asymmetric carbon atoms. This invention includes stereoisomers of the compounds (I) in which the absolute configuration of the asymmetric atom(s) is R-configuration or S-configuration, or mixtures thereof. In particular, preferable stereoisomers thereof are those in which both of the carbon atom bonded to hydroxy group and the carbon atom bonded to $R^2$ take R-configuration when $R^1$ and $R^3$ each is hydrogen atom and $R^2$ is methyl group.

The compounds (I) can be prepared in the form of salt. Examples of the salts are those with inorganic acids such as the hydrochloride, hydrobromide, sulfate, nitrate or phosphate; with organic acids such as the acetate, tartrate, citrate, fumate, maleate, toluenesulfonate or methanesulfonate; with inorganic bases such as the sodium salt, potassium salt, calcium salt or aluminum salt; or with organic bases such as the triethylamine salt, guanidine salt, ammonium salt, hydrazine salt, quinine salt or cinchonine salt.

The compounds (I) thus produced can be separated and purified from the reaction mixture by any conventional methods such as extraction, concentration, neutralization, filtration, recrystallization, column chromatography or thin-layer chromatography.

Each of the compounds (I) can exist in the form of at least two stereoisomers. The invention includes individual isomers or mixtures thereof. These isomers can be prepared stereoselectively by using a single stereoisomer of the starting material (e.g.,(II), (III), (IV) and (V)) in the above mentioned methods. Further, when the products contain two or more kinds of isomers, they can be resolved into a single isomer by conventional resolution methods (e.g., using the formation of their salts with an optically active acid such as camphorsulfonic acid or tartaric acid, other resolution techniques such as various kinds of chromatography or fractional recrystallization).

The compounds (I) if desired can be converted into the corresponding physiologically or pharmaceutically acceptable salts by adding the above-mentioned inorganic acid salts or organic acid salts, if required.

Among the starting material (II) to be used in the present invention, a compound of the formula (II') wherein $R^1$ and $R^3$ each is a hydrogen atom, $R^2$ is methyl and Ar is 2,4-difluorophenyl can be prepared by the method described by the following reaction scheme with the use of a known compound (VI) (The 8th Medicinal Chemistry Symposium, Gist of Lecture, pp.9-12, 1986, Osaka).

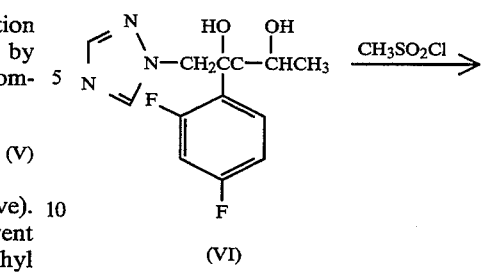

(VI)

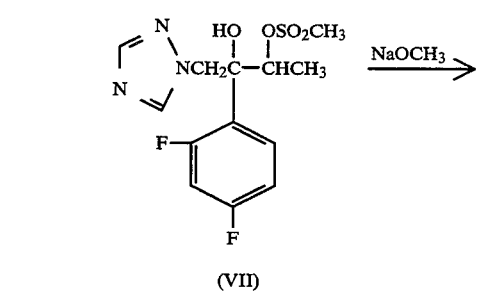

(VII)

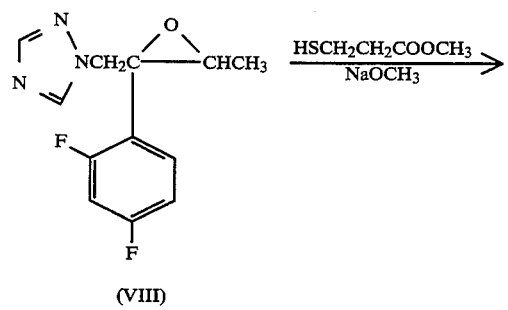

(VIII)

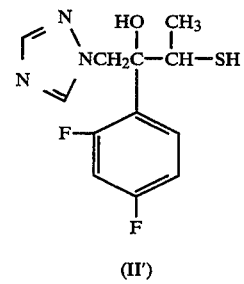

(II')

Activity

Evaluation for fungicidal acitivity of the compound (I) was carried out by the following method.

A paper disk (manufactured by TOYO SEISAKU-SHO, 8mm in diameter) dipped into a methanol solution containing the compound (I) in an amount of 1000 μg/ml was placed on an agar plate containing various fungi. After the cultivation of said fungi for two days at 28° C., mesurement was made to the diameter of a growth inhibiton zone produced around the paper disk. The media used for the evaluation are as follows:

A: Yeast nitrogen base agar (pH 7.0)
B: Sabouraud's agar

Table 2 shows an antifungal spectrum of the compounds (1), (2) and (9).

TABLE 2
(antifungal spectrum)

| Test Fungi | Media | Diameter (mm) | | |
|---|---|---|---|---|
| | | Com.No.1 | No.2 | No.9 |
| Candida albicans IFO 0583 | A | 40 | 30 | 25 |
| Candida utilis IFO 0619 | A | 32 | 40 | 20 |
| Aspergillus niger IFO 4066 | A | 28 | 35 | 13 |
| Aspergillus fumigatus IFO 6344 | A | 45 | 50 | 15 |
| Cryptococcus neoformans IFO 0410 | A | 35 | 30 | 20 |
| Trichophyton rubrum IFO 6467 | B | 35 | 40 | 30 |
| Trichophyton methagrophytes IFO 7522 | B | 40 | 48 | 15 |
| Microsporum gypseum IFO 6075 | B | 40 | 48 | 20 |

Table 3 shows a protective effect of the compound (I) against the experimental infection in mice..

Experimental Method

5-Week old Crj:CDF$_1$ mice were inoculated with the minimum lethal dose of Candida albicans in its vein or abdominal cavity. A drug was administered once immediately after the infection or twice, i.e., immediately after and two hours after the infection. The drug effect was shown with ED50 value calculated by Reed and Muench method from the survival ratio on day 7 after infection. The ED50 value was calculated from the total dose.

TABLE 3

| Compound No. | ED$_{50}$(mg/Kg) |
|---|---|
| 1 | 2.0(S.C.) |
| 2 | 0.5(P.O.) |
| 9 | 2.0(P.O.) |

S.C.: subcutaneous administration
P.O.: oral administration

As apparent from the above, the compound of the invention is low in toxicity, has a potent antifungal effect and a broad antifungal spectrum. Therefore, the compound of the invention can be used for preventing and treating fungus infectious disease of human beings, livestocks or poultry.

The compound of the invention can also be used as an agricultural antifungal agent.

Table 4 shows the effect of the compounds of the present invention used as an agricultural antifungal agent.

Experimental Method 1 Experiment for preventive effect against powdery mildew of barley (Erysiphe graminis)

The compound of the present invention was dissolved in dimethylformamide (end concentration:1 wt. %), to which xylene (end concentration:0.02 wt. %) and Tween 20 ®(end concentration:0.02 wt. %) were added. The resultant solution was diluted with water to obtain a predetermined concentration of the active ingredient. To this diluted solution was added a sticker Dyne ®[manufactured by Takeda Chemical Industries, Ltd., and including polyoxyethylenenonylphenylether (10 wt. %) and potassium ligninsulfonate (10 wt. %)] in a ratio of 0.03 wt. % (end concentration) to prepare a spray. Thus obtained spray was sprayed to a barley seedling (about one week seeding) such that the spray was dripped from the seedling. After air-drying, the spore of susceptible leaf with Erysiphe graminis was forcibly deposited for inoculation. The spore was maintained at an artificial inoculation chamber at a temperature of 20° C. for 8 days after the inoculation. Thereafter, the area rate of lesion was examined to represent the preventive value by the following coefficient.

Preventive value 3: area rate of lesion 0–10%
Preventive value 2: area rate of lesion 11–20%
Preventive value 1: area rate of lesion 21–50%
Preventive value 0: area rate of lesion 51% or more Experimental Method 2 Experiment for preventive effect against blast of rice (Pyricularia oryzae)

A spray containing a predetermined concentration was prepared from the compound of the present invention by the method as described in Experimental Method 1, and sprayed to rice seedling (3 to 4 leaf stages) such that the spray dripped from the seedling. After air-drying, a blast-infested leaf was put between the sprayed rice seedlings to effect inoculation for 24 hours from a susceptible leaf with natural infection. The infected leaf was maintained at a moist chamber at 25° C. to 28° C. for 6 days after the inoculation. Thereafter, the area rate of lesion was examined to represent the preventive value by the following coefficient.

Preventive value 3: area rate of lesion 0–14%
Preventive value 2: area rate of lesion 15–29%
Preventive value 1: area rate of lesion 30–55%
Preventive value 0: area rate of lesion 56% or more

TABLE 4

| Com.No. | Conc. (ppm) | Preventive Value for Erysiphe graminis | Preventive Value for Pyricularia oryzae |
|---|---|---|---|
| 1 | 200 | 3 | 3 |
| 2 | 200 | 3 | 3 |

The compound (I) or its salt can safely be administered to human beings per se or in the form of a pharmaceutically acceptable composition in admixtures with a carrier, excipient or diluent. The phamaceutical composition may take the form of powders, granules, tablets, capsules or injections, and may be administered orally or parenterally.

A daily dosage of the present compound depends upon the state of the infection or administration route. In the case of oral administration, the daily dosage for an adult human lies in a range of about 0.1 mg/Kg per day to about 100 mg/Kg per day, preferably about 1 mg/Kg per day to about 50 mg/Kg per day, in order to treat the infectious disease.

Moreover, the compound (I) or its salt can be used as an external disinfectant. For example, an ointment can be prepared from the compound of the invention with petrolatum or lanolin as the raw material. Said ointment contains the compound of the invention in an amount of about 0.1 to 100 mg per 1 g and can be used for sterilizing and disinfecting skin or muscous membrane.

In addition, the compound (I) or its salt can be formulated as agricultural compositions (e.g., dusts, microgranules, meltable powders, emulsifiable concentrates, suspensions or aerosols) in accordance with the conventional techniques.

The invention is further illustrated by the following examples, by which no limitation shall not be given.

Reference Example 1

(2RS,3RS)-2-(2,4-difluorophenyl)-1-(1H-1,2,4-triazol-1-yl)-2,3-butanediol (11 g) was dissolved in a mixture of ethyl acetate (200 ml) and methylene chloride (50 ml), to which triethylamine (6.21 ml) was added under ice-cooling. Then, methanesulfonyl chloride (3.46 ml) was added dropwise to the mixture over the period of 3 minutes under ice-cooling and stirring. After the addition, the resultant solution was stirred for 45 minutes at room temperature. Thereafter, water (100 ml) was added to the solution to separate the organic layer. The organic layer was washed with water, dried over anhydrous magnesium sulfate and distilled off to remove the solvent under reduced pressure, obtaining (2RS,3RS)-2-(2,4-difluorophenyl)-3-methanesulfonyloxy-1-(1H-1,2,4-triazol-1-yl)-2-butanol as an oil. Thus obtained compound was dissolved in methanol (200 ml), to which a sodium methylate methanolic solution (8.84 g, 28%) was added under ice-cooling. The resultant solution was stirred for 30 minutes at room temperature. The solvent was removed under reduced pressure, and the residue was extracted with ethyl acetate (200 ml) and water (100 ml). The ethyl acetate layer was washed with water, dried over anhydrous magnesium sulfate and distilled off the solvent under reduced pressure. The residue was purified by a silica gel column chromatography (ethyl acetate-methylene chloride=4:1) and crystallized from hexane to give (2RS,3SR)-2-(2,4-difluorophenyl)-3-methyl-2-(1H-1,2,4-triazol-1-yl)methyloxirane (8.3 g) as colorless crystals which was a single diastereomer.

mp: 66°–68° C.

$^1$H-NMR(CDCl$_3$)$\delta$: 1.65(3H,d,J=5.6 Hz), 3.20(1H,q,J=5.6 Hz), 4.42(1H,d,J=14.6 Hz), 4.89(1H,d,J=14.6 Hz),6.68–6.83(2H,m), 6.93–7.08(1H,m), 7.82 (1H,s), 7.97 (1H,s)

Elemental Analysis for C$_{12}$H$_{11}$F$_2$N$_3$ O Calcd. (%): C, 57.37; H, 4.41; N, 16.73 Found (%): C, 57.31; H, 4.44; N, 16.62

Reference Example 2

(2R,3R)-2-(2,4-difluorophenyl)-1-(1H-1,2,4-triazol-1-yl)-2,3-butanediol (1.25 g) was dissolved in a mixture of ethyl acetate (40 ml) and dichloromethane (10 ml), to which triethylamine (0.84 ml) and methanesulfonyl chloride (0.48 ml) were added under ice-cooling. The resultant solution was stirred for 30 minutes at room temperature. After adding ethyl acetate, the reaction mixture was washed with water, dried over anhydrous magnesium sulfate and concentrated to obtain (2R,3R)-2-(2,4-difluorophenyl)-3-methanesulfonyloxy-1-(1H-1,2,4-triazol-1-yl)-2-butanol as an oil. Thus obtained compound was dissolved in methanol (40 ml), to which sodium methylate methanolic solution (1.16 ml, 28%) was added under ice-cooling. The resultant solution was stirred for 30 minutes at room temperature. The reaction mixture was concentrated to about 10 ml under reduced pressure, and the residue was extracted with ethyl acetate (100 ml). The ethyl acetate layer was washed with water, dried over anhydrous magnesium sulfate and distilled off the solvent under reduced pressure. The residue was subjected to a silica gel column chromatography (ethyl acetate- dichloromethane=4:1) for purification and then recrystallized from a mixture of ethyl acetate and hexane to give (2R,3S)-2-(2,4-difluorophenyl)-3-methyl-2-[(1H-1,2,4-triazol-1-yl)methyl]oxirane (520 mg) as colorless needles.

mp: 89°–90° C.

$[\alpha]_D^{23} = -8.3°$ (c=1.0 in MeOH)

$^1$H-NMR(CDCl$_3$) $\delta$: 1.65(3H,d,J=5.6 Hz), 3.20(1H,q,J=5.6 Hz), 4.43(1H,d,J=14.6 Hz), 4.88(1H,d,J=14.6 Hz),6.68–6.83(2H,m), 6.93–7.08(1H,m), 7.82(1H,s), 7.97(1H,s)

Elemental Analysis for C$_{12}$H$_{11}$F$_2$N$_3$Calcd. (%): C, 57.37; H, 4.41; N, 16.73 Found (%): C, 57.27; H, 4.43; N, 16.83

The above product was analyzed by a high-performance liquid chromatography (mobil phase: hexane:isopropyl alcohol=9:1) using an optical resolution column (CHIRALCEL ® OF 0.46cm×25cm, Daicel Chemical Industries, Ltd.). The enantiomer excess of the above product was 99.2%.

Reference Example 3

A solution of (2RS,3SR)-2-(2,4-difluorophenyl)-3-methyl-2-(1H-1,2,4-triazol-1-yl)methyloxirane (7.0 g), methyl 3-mercaptopropionate (30.8 ml) and 28% sodium methylate-methanol solution (19.6 ml) in methanol (210 ml) was refluxed for 2 hours. 28% Sodium methylate methanolic solution (9.8 ml) was added to the resultant solution and refluxed for 1 hour. Thereafter, methyl 3-mercaptopropionate (4 ml) was added to the resultant solution and refluxed for 2 hours. After ice-cooling, the reaction mixture was diluted with water (100 ml) and neutralized with 5% aqueous phosphate solution, and extracted with methylene chloride (200 ml×2). The extract was dried over anhydrous sodium sulfate and distilled off the solvent under reduced pressure. The residue was subjected to a silica gel column chromatography (4×50cm), eluting with ethyl acetate-hexane (3:1). The collected fractions of the object compound were concentrated and ethyl ether was added to the residue to obtain (2RS,3RS)-2-(2,4-difluorophenyl)-3-mercapto-1-(1H-1,2,4-triazol-1-yl)-2butanol (5.5 g) as colorless needles.

$^1$H-NMR(CDCl$_3$)$\delta$: 1.17(3H,d,J=7.0 Hz), 1.96(1H,d,J=10.2 Hz), 3.45(1H,d,q,J=7.0 Hz,J=10.2 Hz), 4.77(1H,s),4.82(1H,d,J=14.4 Hz), 5.01(1H,d,J=14.4 Hz), 6.70–6.81(2H,m), 7.33–7.45(1H,m),7.79(1H,s),7.80(1H,s)

The product (1.5 g) was recrystallized from ethyl acetate (20 ml) to obtain colorless prisms (0.6 g).

mp: 145°–147° C.

Reference Example 4

A solution of (2R,3S)-2-(2,4-difluorophenyl)-3-methyl-2-[(1H-1,2,4-triazol-1-yl)methyl]oxirane (0.40 g), methyl 3-mercaptopropionate (1.42 ml) and 28% sodium methylate methanolic solution (1.25 ml) in methanol (10 ml) was refluxed for 4.5 hours in an oil bath under heating. To the reaction mixture was added methyl 3-mercaptopropionate (0.53 ml, 0.32 ml) respectively after 2 hours and 3.5 hours of heating. Further, 28% sodium methylate-methanol solution (0.63 ml) was added after 2.5 hours. After 4.5 hours, the reaction mixture was cooled, neutralized with 1N hydrochloric acid (9.6 ml) and extracted with dichloromethane (100 ml). The extract was washed with saturated saline (20 ml), dried over anhydrous sodium sulfate and distilled off the solvent under reduced pressure. The residue was subjected to a silica gel column chromatography (hexane:ethyl acetate=1:3) for purification. The objective fractions were concentrated. Then, the collected precipitate was washed with isopropyl ether to afford (2R, 3R)-2-(2,4-difluorophenyl )-3-mercapto-1-(1-H-1,2,4-triazol-1-yl)-2-butanol (0.22 g) as colorless needles.

mp: 176°–178° C.

$[\alpha]_D^{23} = -56.8°$ (c=0.7 in methanol)

Elemental Analysis for $C_{12}H_{13}F_2N_3OS$ Calcd. (%): C, 50.52; H, 4.59; N, 14.73 Found (%): C, 50.81; H, 4.64; N, 14.64

$^1$H-NMR(CDCl$_3$)δ: 1.17(3H,d,J=7.0 Hz), 1.96(1H,d,J=10.2 Hz), 3.45(1H,m), 4.76(1H,s),4.82(1H,d,J=14.4 Hz), 5.01(1H,d,J=14.4 Hz), 6.74(2H,m),7.33–7.45(1H,m), 7.79(2H,s)

In order to measure the enantiomer excess (ee), the product was converted into the (2R,3R)-S-acetyl compound, which was analyzed by a high-performance liquid chromatography (mobil phase: hexane:isopropyl alcohol=7:3) using an optical resolution column (CHIRALCEL® OF 0.46cm×25 cm, Daisel Chemical Industries, Ltd.). The (2R,3R)-S-acetyl compound showed a single peak at the retention time of 17 minutes at a rate of flow of 1 ml/min. Its enantiomer excess was 99.7%.

[The corresponding racemate (i.e., the S-acetyl derivative of the compound prepared in Example 3) showed two peaks having an area ratio of 1:1 at the retention time of 10 minutes and 17 minutes respectively.]

EXAMPLE 1

(2RS,3RS)-2-(2,4-difluorophenyl)-3-mercapto-1-[1H-1,2,4-triazol-1-yl]-2-butanol (0.3 g) was added to dichloromethane (5 ml), to which triethylamine (0.16 ml) was added under ice-cooling, and then, N,N-diethylthiocarbamoyl chloride (0.18 g) was added. The resultant solution was stirred for 1 hour at room temperature. Thereafter, water (20 ml) was added to the reaction mixture. The resultant mixture was then extracted with dichloromethane (40 ml). The extract was washed with water (20 ml), dried (MgSO$_4$) and distilled off to remove the solvent under reduced pressure. The residue was purified by a silica gel column chromatography (2.9×30cm, eluent: ethyl acetate-dichloromethane=1:3). The objective fractions were concentrated. Hexane was added to the residue to give the compound (1), i.e., [(2RS,3RS)-3-(2,4-difluorophenyl)-3-hydroxy-4-(1H-1,2,4-triazol-1-yl)-2butyl] N,N-diethyldithiocarbamate (0.13 g) as colorless needles.

mp: 102°–104 ° C.

$^1$H-NMR(CDCl$_3$) δ: 1.21(3H,d,J=7.4 Hz), 1.24–1.37 (6H,m), 3.84(2H,q,J=7 Hz), 4.08(2H,q,J=7 Hz), 4.83(1H,d,J=14 Hz), 5.10–5.24(3H,m), 6.71–6.84(2H,m) 7.36–7.48(1H,m),7.78(1H,s), 7.81(1H,s)

Elemental Analysis for $C_{17}H_{22}F_2N_4OS_2$ Calcd. (%): C, 50.98; H, 5.54; N, 13.99 Found (%): C, 51.29; H, 5.55; N, 14.02

EXAMPLE 2

(2R,3R)-2-(2,4-difluorophenyl)-3-mercapto-1-[1H-1,2,4-triazol-1-yl]-2-butanol (0.6 g) was added to dichloromethane (10 ml), to which triethylamine (0.32 ml) was added under ice-cooling, and then, N,N-diethylthiocarbamoyl chloride (0.7 g) was added. The resultant solution was stirred for 10 hours at room temperature. Thereafter, water (20 ml) was added to the mixture. The resultant mixture was then extracted with dichloromethane (30 ml). The extract was washed with water (20 ml), dried (MgSO$_4$) and distilled off to remove the solvent under reduced pressure. The residue was purified by a silica gel column chromatography (2.9×25cm, eluent: ethyl acetate-dichloromethane=1:3). The objective fractions were concentrated. The residue was treated with hydrogen chloride-ethyl acetate solution to give the hydrochloride of the compound (2), i.e., [(2R,3R)-3-(2,4-difluorophenyl)-3-hydroxy-4-(1H-1,2,4-triazol-1-yl)-2-butyl] N,N-diethyldithiocarbamate hydrochloride (0.12 g) as colorless needles.

mp: 154°–156 ° C.

$^1$H-NMR(DMSO-d$_6$) δ: 1.10(3H,d,J=7 Hz), 1.15–1.33(6H,m), 3.81(2H,q,J=7 Hz), 4.01(2H,q,J=7 Hz), 4.81(2H,s), 5.09(1H,q,J=7 Hz), 6.86–6.96(1H,m) 7.14–7.30(2H,m),7.85(1H,s), 8.63(1H,s)

Elemental Analysis for $C_{17}H_{22}F_2N_4OS_2 \cdot HCl$ Calcd. (%): C, 46.73; H, 5.30; N, 12.82 Found (%): C, 46.65; H, 5.32; N, 12.60

EXAMPLE 3

N-Methyl-m-toluidine (0.6 g) and thiophosgen (0.38 ml) were dissolved in chloroform (10 ml), to which 10% aqueous sodium hydroxide solution (2.4 ml) was added dropwise under ice-cooling and stirring. After the addition, the resultant solution was stirred for 5 hours at room temperature. The chloroform layer was collected and dried (MgSO$_4$), to which (2R,3R)-2-(2,4-difluorophenyl)-3-1-mercapto-1-[1H-1,2,4-triazol-1-yl]-2-butanol (0.2 g) and triethylamine (0.11 ml) were added. This mixture was stirred for 10 hours at room temperature, diluted with water (15 ml) and then extracted with chloroform (20 ml). The extract was washed with water (15 ml), dried (MgSO$_4$) and distilled off the solvent under reduced pressure. The residue was purified by a silica gel column chromatography (2.9×15cm, eluent: dichloromethane:ethyl acetate=1:4). The objective fractions were concentrated and the residue was treated with hydrogen chloride-ethyl acetate solution to afford the hydrochloride of the compound (9), i.e., [(2R,3R)-3-(2,4-difluorophenyl)-3-hydroxy-4-(1H,1,2,4-triazol-1-yl)-2-butyl] N-methyl-N-(3-methylphenyl) dithiocarbamate hydrochloride (0.006 g) as colorless needles.

mp: 161°–163 ° C.

$^1$H-NMR(DMSO-d$_6$) δ: 1.02(3H,d,J=7.2 Hz), 2.39(3H,s), 3.73(3H,s), 4.66(1H,d,J=14 Hz), 4.80(1H,d,J=14 Hz), 5.02(1H,q,J=7.2 Hz), 6.81–6.91(1H,m), 7.08–7.48(6H,m), 7.77(1H,s), 8.47(1H,s)

Elemental Analysis for $C_{21}H_{22}F_2N_4OS_2 \cdot HCl \cdot 0.5H_2O$ Calcd. (%): C, 51.06; H, 4.90; N, 11.34 Found (%): C, 51.30; H, 4.90; N, 11.11

EXAMPLE 4

Morpholine (0.91 g) and thiophosgen (0.8 ml) were dissolved in chloroform (25 ml), to which 10% aqueous sodium hydroxide solution (5 ml) was added dropwise under ice-cooling and stirring. After the addition, the resultant solution was stirred for 3 hours at room temperature. The chloroform layer was collected, dried (MgSO$_4$) and distilled off the solvent under reduced pressure. The residue was dissolved in methanol (5 ml) for use in the next step.

(2R,3R)-2-(2,4-Difluorophenyl)-3-mercapto-1-[1H-1,2,4-triazol-1-yl]-2-butanol (1.0 g) was dissolved in methanol (15 ml), to which 28% sodium methylate methanolic solution (0.67 g) was added. Thereafter, the methanolic solution of the thiocarbamoyl chloride compound prepared above was added to the resultant solution, followed by stirring for 1 hour at room temperature. Then, water (20 ml) was added to the reaction mixture which was then extracted with dichloromethane (40 ml×2). The extract was washed with water (40 ml), dried (MgSO$_4$) and distilled off the solvent under reduced pressure. The residue was purified by a silica gel column chromatography (2.9×40cm, eluent: ethyl acetate:dichloromethane=1:3–3:1). The collected corresponding fractions were concentrated to afford the compound (4), i.e., [(2R,3R)-3-(2,4-difluorophenyl)-3-hydroxy-4-(1H-1,2,4-triazol-1-yl)-2butyl] 1-morpholinecarbodithiolate (0.24 g) as a colorless oil.

$^1$H-NMR(CDCl$_3$) δ: 1.21(3H,d,J=7.2 Hz), 3.74–3.82(4H,m), 4.02–4.41(4H,m), 4.82(1H,d,J=14.6 Hz), 5.11(1H,d,J=14.6 Hz), 5.17–5.24(2H,m), 6.71–6.84(2H,m), 7.33–7.46(1H,m), 7.81(2H,s)

EXAMPLE 5

Indoline hydrochloride (0.81 g) and triethylamine (1.46 ml) were dissolved in chloroform (15 ml), to which thiophosgen (0.4 ml) was added under ice-cooling and stirring. After the addition, the resultant solution was stirred for 30 minutes at room temperature. Thereafter, (2R,3R)-2-(2,4-difluorophenyl)-3-mercapto-1-[1H-1,2,4-triazol-1-yl]-2-butanol (0.5 g) and triethylamine (0.48 ml) were added and the resultant mixture was stirred for 2 hours at room temperature. Then, water (10 ml) was added to the reaction mixture which was then extracted with chloroform (5 ml). The extract was washed with water (10 ml), dried (MgSO$_4$) and distilled off the solvent under reduced pressure. The residue was purified by a silica gel column chromatography (2.9'40cm, eluent: dichloromethane:ethyl acetate=15:1–5:1). The collected corresponding fractions were concentrated to afford the compound (16), i.e., [(2R,3R)-3-(2,4-difluorophenyl)-3-hydroxy-4-(1H-1,2,4-triazol-1-yl)-2-butyl] 1-indolinecarbodithiolate (0.27 g) as a pale brown oil.

$^1$H-NMR(CDCl$_3$) δ: 1.25(3H,d,J=7.4 Hz), 3.23(2H,t,J=8 Hz), 4.59(2H,t,J=8 Hz), 4.87(1H,d,J=14.2 Hz), 5.15(1H,d,J=14.2 Hz), 5.24–5.38(2H,m), 6.73–6.84(2H,m), 7.11–7.49(5H,m), 7.79(2H,s)

EXAMPLE 6

(2R,3R)-2-(2,4-difluorophenyl)-3-mercapto-1-[1H-1,2,4-triazol-1-yl]-2-butanol (0.67g) was dissolved in dichloromethane (15 ml), to which phenyl isothiocyanate (0.32 g) was added at room temperature. Then, triethylamine (0.36 ml) was added to the resultant solution, which was left for 60 hours at room temperature. Thereafter, water (10 ml) was added to the mixture, which was then extracted with dichloromethane (5 ml). The extract was washed with water (10 ml), dried (MgSO$_4$) and distilled off the solvent under reduced pressure. The residue was purified by a silica gel column chromatography (2.9×40cm, eluent: dichloromethane:ethyl acetate=3:2). The collected corresponding fractions were concentrated to afford the compound (14), i.e., [(2R,3R)-3-(2,4-difluorophenyl)-3-hydroxy-4-(1H,1,2,4-triazol-1-yl)-2-butyl] N-phenyldithiocarbamate (0.43 g) as a pale yellow oil. 1H-NMR(CDCl$_3$) δ: 1.23(3H,d,J=7.2 Hz), 4.84(1H,d,J=14.2 Hz), 4.98–5.30(2H,m), 5.12(1H,d,J=14.2 Hz), 6.71–6.83(2H,m), 7.35–7.57(6H,m), 7.79(1H,s), 7.80(1H,s), 9.18(1H,s)

EXAMPLE 7 p-Trifluoromethylaniline (0.85 g) was allowed to react with thiophosgen (0.4 ml), followed by the reaction with (2R,3R)-2-(2,4-difluorophenyl)-3-mercapto-1-[1H-1,2,4-triazol-1-yl]-2-butanol (0.5 g) by the same manner as in Example 5. The compound (21), i.e., [(2R,3R)-3-(2,4-difluorophenyl)-3-hydroxy-4-(1H,1,2,4-triazol-1-yl)-2butyl] N-(4-trifluoromethylphenyl)dithiocarbamate (0.31 g) was obtained as a pale yellow oil.

$^1$H-NMR(CDCl$_3$) δ: 1.26(3H,d,J=7.2 Hz), 4.79–4.87(1H,m), 4.86(1H,d,J=14.2 Hz), 5.11(1H,d,J=14.2 Hz), 5.48(1H,bs) 6.74–6.86(2H,m), 7.34–7.46(1H,m), 7.60–7.81(4H,m), 7.82(2H,s), 9.31(1H,s)

EXAMPLE 8

Methyl anthranilate (0.79 g) was allowed to react with thiophosgen (0.4 ml), followed by the reaction with (2R,3R)-2-(2,4-difluorophenyl)-3-mercapto-1-[1H-1,2,4-triazol-1-yl]-2-butanol (0.5 g) by the same manner as in Example 5. The compound (17), i.e., [(2R,3R)-3-(2,4-difluorophenyl)-3-hydroxy-4-(1H,1,2,4-triazol-1-yl)-2-butyl] N-(2-methoxycarbonylphenyl)dithiocarbamate (0.49 g) was obtained as a pale yellow oil.

$^1$H-NMR(CDCl$_3$) δ: 1.26(3H,d,J=7.2 Hz), 3.98(3H,s), 4.90(1H,d,J=14.2 Hz), 4.89–5.02(1H,m), 5.10(1H,d,J=14.2 Hz), 5.19(1H,bs), 6.72–6.84(2H,m), 7.19–7.65(3H,m), 7.80(2H,s), 8.11(1H,dd,J=8 Hz), 9.21(1H,d,J=8.4 Hz), 12.38(1H,s)

EXAMPLE 9

2,3-Difluoroaniline (0.68 g) was allowed to react with thiophosgen (0.4 ml), followed by the reaction with (2R, 3R)- 2-(2,4-difluorophenyl)- 3-mercapto-1-[1H-1,2,4-triazol-1-yl]-2-butanol (0.5 g) by the same manner as in Example 5. The compound (18), i.e., [(2R,3R)-3-(2,4-difluorophenyl)-3-hydroxy-4-(1H,1,2,4-triazol-1-yl)-2-butyl] N-(2,3-difluorophenyl)dithiocarbamate (0.26 g) was obtained as a pale yellow oil.

$^1$H-NMR(CDCl$_3$) δ: 1.26(3H,d,J=7.2 Hz), 4.76–4.88(1H,m), 4.85(1H,d,J=14.4 Hz), 4.88(1H,d,J=14.4 Hz), 5.45(1H,s), 6.69–6.84(2H,m), 7.08–7.19(2H,m), 7.32–7.45(1H,m), 7.78–7.91(1H,m), 7.80(2H,s), 9.10(1H,s)

EXAMPLE 10

To a solution of phenethylamine (3.06 g) and thiophosgen (1.9 ml) in chloroform (45 ml) was added gradually 10% aqueous sodium hydroxide solution (12.8 ml) at 0° C. The mixture was vigorously stirred for 3 hours at room temperature. The chloroform layer was dried over anhydrous magnesium sulfate and filtered. To the filtrate were added (2R,3R)-2-(2,4-difluorophenyl)-3-mercapto-1-[1H-1,2,4-triazol-1-yl]-2-butanol (1.0 g) and triethylamine (0.54 ml) at room temperature. The mixture was allowed to stand for 15 hours at room temperature. The reaction mixture was washed with water (40 ml), dried over anhydrous sodium sulfate and concentrated under reduced pressure. The residue was purified by a silica gel column chromatography (2.5×15cm, ethyl acetate:hexane=1:1). The objective fractions were concentrated. Diethyl ether was added to the residue to remove insoluble materials (0.10 g). The filtrate was subjected to a silica gel column chromatography (1.0×15cm, methylene chloride:acetone=10:0.5). The collected corresponding fractions were concentrated to afford the compound (22), i.e., [(2R,3R)-3-(2,4-difluorophenyl)-3-hydroxy-4-(1H-1,2,4-triazol-1-yl)-2-butyl] N-(2-phenylethyl)dithiocarbamate (0.25 g) as a colorless oil.

$^1$H-NMR(CDCl$_3$) δ: 1.18(3H,d,J=7.2 Hz), 3.00(2H,t,J=7.0 Hz), 4.02(2H,m), 4.76(1H,q,J=7.2 Hz), 4.77(1H,d,J=14.4 Hz), 5.06(1H,d,J=14.4 Hz), 5.26(1H,s), 6.65–6.83(2H,m), 7.10–7.40(6H,m), 7.75(1H,s), 7.85(1H,br)

EXAMPLE 11

A solution of di-n-butylamine (2.2 ml) in hexane (4.0 ml) was added gradually to a solution of thiophosgen (0.50 ml) in hexane (20 ml) at 0° C. After two hours, the precipitated white solids were filtered off, and the filtrate was concentrated under reduced pressure. The residue was dissolved in dichloromethane (18 ml), to which (2R,3R)-2-(2,4-difluorophenyl)-3-mercapto-1-[1H-1,2,4-triazol-1-yl]-2-butanol (0.60 g) was added at room temperature and further triethylamine (0.30 ml) was added at −20° C. The resultant mixture was left for 60 hours at 0° C. The reaction mixture was washed with water (20 ml), dried over anhydrous sodium sulfate and concentrated under reduced pressure. The residue was purified by a silica gel column chromatography (2.5×15cm, ethyl acetate:hexane=1:2). The collected corresponding fractions were concentrated. The residue was subjected twice to a silica gel column chromatography (1.0×15cm, methylene chloride: methanol=100:0.5). The collected corresponding fractions were concentrated to afford the compound (13), i.e., [(2R,3R)-3-(2,4-difluorophenyl)-3-hydroxy-4-(1H-1,2,4-triazol-1-yl)-2-butyl] N,N-dibutyldithiocarbamate (0.035 g) as a colorless oil.

$^1$H-NMR(CDCl$_3$) δ: 0.9–1.1(6H,m), 1.20(3H,d,J=7.4 Hz), 1.3–1.8(8H,m), 3.73(2H,m), 3.98(2H,m), 4.80(1H,d,J=14.2 Hz), 5.13(1H,d,J=14.2 Hz), 5.14(1H,q,J=7.4 Hz), 5.20(1H,d,J=1.4 Hz), 6.7–6.85(2H,m), 7.35–7.47(1H,m), 7.79(1H,s), 7.81(1H,s)

EXAMPLE 12

Diethyl ether (13 ml) containing piperidine (1.31 ml) was added at −78° C. to diethyl ether (10 ml) containing thiophosgen (0.5 ml) during 10 minutes under stirring. After stirring for 1 hour at −78° C., the resultant mixture was warmed to room temperature and then filtered to remove the precipitated white solids. The filtrate was concentrated under reduced pressure, to which methylene chloride (30 ml) was added. The resultant solution was cooled to 0° C., to which (2R,3R)-2-(2,4-difluorophenyl)-3-mercapto-1-[1H-1,2,4-triazol-1-yl]-2-butanol (0.93 g) and triethylamine (0.46 ml) were added. The mixture was stirred for 4 hours at room temperature. The reaction mixture was washed with water (10 ml), dried over anhydrous sodium sulfate and concentrated under reduced pressure. The residue was purified by a silica gel column chromatography (2.5×25cm, ethyl acetate:hexane=1:1). The collected corresponding fractions were concentrated to afford the compound (11), i.e., [(2R,3R)-3-(2,4-difluorophenyl)-3-hydroxy-4-(1H-1,2,4-triazol-1-yl)-2butyl] 1-piperidinecarbodithiolate (0.22 g) as a pale yellow oil.

$^1$H-NMR(CDCl$_3$) δ: 1.20(3H,d,J=7.4 Hz), 1.6–1.8(6H,m), 3.9–4.4(4H,m), 4.82(1H,d,J=13.8 Hz), 5.11(1H,d,J=13.8 Hz), 5.15 (1H,q,J=7.4 Hz), 5.20(1H,d,J=1.6 Hz), 6.7–6.85(2H,m), 7.34–7.47(1H,m), 7.78(1H,s), 7.79(1H,s)

EXAMPLE 13

Diethyl ether (13 ml) containing N-phenylpiperazine (1.4 ml) was added at −50° C. to diethyl ether (10 ml) containing thiophosgen (0.5 ml) during 15 minutes under stirring. After stirring for 1.7 hours at −50° C., the mixture was warmed to room temperature and then filterd to remove the precipitated white solids. The filtrate was concentrated under reduced pressure, to which methylene chloride (30 ml) was added. The resultant solution was cooled to 0° C., to which (2R,3R)-2-(2,4-difluorophenyl)-3-mercapto-1-[1H-1,2,4-triazol-1-yl]-2-butanol (0.93 g) and triethylamine (0.46 ml) were added. The resultant mixture was stirred for 3 hours at room temperature. The reaction mixture was washed with water (10 ml), dried over anhydrous sodium sulfate and concentrated under reduced pressure. The residue was purified by a silica gel column chromatography (2.5×25cm, ethyl acetate:hexane=1:1). The collected corresponding fractions were concentrated to afford the compound (8), i.e., [(2R,3R)-3-(2,4-difluorophenyl)-3-hydroxy-4-(1H-1,2,4-triazol-1-yl)-2butyl] 1-(4-phenylpiperazine)carbodithiolate (0.93 g) as colorless oil.

$^1$H-NMR(CDCl$_3$) δ: 1.22(3H,d,J=7.2 Hz), 3.31–3.37(4H,m), 4.1–4.7(4H,m), 4.84(1H,d,J=14.4 Hz), 5.13(1H,d,J=14.4 Hz), 5.19(1H,q,J=7.2 Hz), 5.26(1H,d,J=1.8 Hz), 6.7–7.0(5H,m), 7.26–7.47(3H,m), 7.80(2H,s),

EXAMPLE 14

Diethyl ether (13 ml) containing 2,6-dimethylmorpholine (cis-trans mixture.) (1.6 ml) was added at −50° C. to diethyl ether (10 ml) containing thiophosgen (0.5 ml) during 15 minutes under stirring. After stirring for 1.7 hours at −50° C., the mixture was warmed to room temperature and then filtered to remove the precipitated white solids. The filtrate was concentrated under reduced pressure, to which methylene chloride (30 ml) was added. The resultant mixture was cooled to 0° C., to which (2R,3R)-2-(2,4-difluorophenyl)-3-mercapto-1-[1H-1,2,4-triazol-1-yl]-2-butanol (0.93 g) and triethylamine (0.46 ml) were added. The mixture was stirred for 15 hours at room temperature. The reaction mixture was washed with water (10 ml), dried over anhydrous sodium sulfate and concentrated under reduced pressure. The residue was purified by a silica gel column chromatography (2.5×25cm, ethyl acetate:n-hexane=1:1). The collected corresponding fractions were concentrated to afford the compound (10), i.e., [(2R,3R)-3-(2,4-difluorophenyl)-3-hydroxy-4-(1H-1,2,4-triazol-1-yl)-2-butyl] 3,5-dimethylmorpholine-1carbodithiolate (0.91 g) as a colorless oil.

$^1$H-NMR(CDCl$_3$) δ: 1.1–1.3(9H,m), 2.7–3.1(2H,m), 3.6–3.8(2H,m), 4.5–4.7(1H,m), 4.80(1H, d,J=14.2 Hz), 5.10(1H, d,J=14.2 Hz), 5.19 (1H,q,J=7.4 Hz), 5.26(1H,d,J=1.6 Hz), 5.4–5.6(1H,m), 6.7–6.9(2H,m), 7.3–7.5(1H,m), 7.78(1H,s), 7.79(1H,s)

EXAMPLE 15

2,4-Dichloroaniline (0.85 g) was allowed to react with thiophosgen (0.4 ml), followed by the reaction with (2R,3R)-2-(2,4-difluorophenyl)-3-mercapto-1-[1H-1,2,4-triazol-1-yl]-2-butanol (0.5 g) by the same manner as in Example 5. The compound (23), i.e., [(2R,3R)-3-(2,4-difluorophenyl)-3-hydroxy-4-(1H-1,2,4-triazol-1-yl)-2-butyl] N-(2,4-dichlorophenyl)dithiocarbamate (0.08 g) was obtained as a pale yellow oil.

$^1$H-NMR(CDCl$_3$) δ: 1.24(3H,d,J=7.0 Hz), 4.80–4.99(1H,m), 4.84(1H,d,J=14.4 Hz), 5.11(1H,d,J=14.4 Hz), 5.36(1H,s), 6.71–6.84(2H,m), 7.29–7.54(3H,m), 7.80(2H,s), 7.97–8.02(1H,m), 9.17(1H,s)

EXAMPLE 16

Diethyl ether (13 ml) containing pyrrolidine (1.1 ml) was added to diethyl ether (10 ml) containing thiophosgen (0.5 ml) during 15 minutes at −50° C. under stirring. After stirring for 1 hour at −50° C., the mixture was warmed to room temperature and then filtered to remove the precipitated white solids. The filtrate was concentrated under reduced pressure, to which diethyl ether was added to remove the insoluble materials. The filtrate was concentrated under reduced pressure. The residue was dissolved in a little amount of diethyl ether and the solution was cooled for 2 hours at 0° C. The precipitated crystals (0.5 g) were collected. The crystals (0.25 g) were dissolved in dichloromethane (8.0 ml), to which (2R,3R)-2-(2,4-difluorophenyl)-3-mercapto-1-[1H-1,2,4-triazol-1-yl]-2-butanol (0.47 g) and triethylamine (0.23 ml) were added at 0° C. The resultant mixture was allowed to stand for 11 hours at room temperature. The reaction mixture was washed with water (10 ml), dried over anhydrous sodium sulfate and concentrated under reduced pressure. The residue was purified by a silica gel column chromatography (2.0×25cm, eluent: dichloromethane: methanol=100:2.5). The collected corresponding fractions were concentrated to afford the compound (31), (2R,3R)-3-(2,4-difluorophenyl)-3-hydroxy-4-(1H-1,2,4-triazol-1-yl)-2-butyl] 1-pyrrolidinecarbodithiolate (0.49 g) as a pale yellow oil.

$^1$H-NMR(CDCl$_3$) δ: 1.21(3H,d,J=7.2 Hz), 1.9-2.2(4H,m), 3.7-4.1(4H,m), 4.85(1H,d,J=14.4 Hz), 5.11(1H,d,J=14.4 Hz), 5.11(1H,q,J=7.2 Hz), 5.21(1H,d,J=1.8 Hz), 6.7-6.9(2H,m), 7.3-7.5(1H,m), 7.79(2H,s)

EXAMPLE 17

(2R,3R)-2-(2,4-difluorophenyl)-3-mercapto1-[1H-1,2,4-triazol-1-yl]-2-butanol (0.10 g) was allowed to react with N,N-dimethylthiocarbamoyl chloride (0.13 g) in dichloromethane (3.0 ml) in the presence of triethylamine (49 ml) by the same manner as in Example 2. The compound (32), i.e., [(2R,3R)-3-(2,4-difluorophenyl)-3-hydroxy-4-(1H-1,2,4-triazol-1-yl)-2-butyl] N,N-dimethyldithiocarbamate (0.08 g) was obtained as colorless oil.

$^1$H-NMR (CDCl$_3$) δ: 1.19(3H,d,J=7.4 Hz), 3.44(3H,s), 3.59(3H,s), 4.82(1H,d,J=14.2 Hz), 5.10(1H,d,J=14.2 Hz), 5.10(1H,q,J=7.4 Hz), 5.22(1H,d,J=1.6 Hz), 6.6-6.9(2H,m), 7.3-7.5(1H,m), 7.79(2H,s)

What we claim is:

1. A triazole compound of the formula (I):

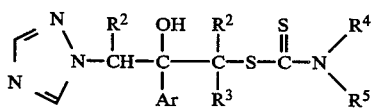

wherein Ar is a phenyl group having 1 to 3 substituents selected from the group consisting of a halogen atom and a trifluoromethyl group R$^1$, R$^2$ and R$^3$ each represents, the same or different, a hydrogen atom or a lower alkyl, R$^4$ and R$^5$ each represents, the same or different, a hydrogen atom, a straight or branched chain alkyl group having 1 to 12 carbon atoms, phenyl-C$_{1-4}$-alkyl, napthyl-C$_{1-4}$-alkyl, phenyl, napthyl, biphenyl, anthryl, or indenyl, or its salt.

2. A compound of claim 1 in which the substituted phenyl group is 2,4-difluorophenyl.

3. A compound of claim 1 in which R$^1$ and R$^3$ are a hydrogen atom and R$^2$ is a lower alkyl group.

4. A compound of claim 1 in which R$^1$ and R$^3$ are a hydrogen atom and R$^2$ is methyl.

5. A triazole compound of the formula (I'):

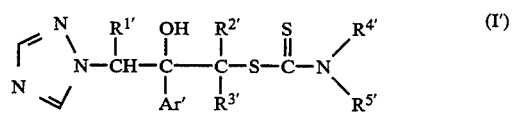

wherein Ar' is a phenyl group having 1 to 3 substituents selected from the group consisting of a halogen atom and a trifluoromethyl group, R$^{1'}$, R$^{2'}$ and R$^{3'}$ each represents, the same or different, a hydrogen atom, a straight or branched chain alkyl group having 1 to 12 carbon atoms, either one of R$^{4'}$ and R$^{5'}$ is a hydrogen atom and the other is a straight or branched chain alkyl group having 1 to 12 carbon atoms; a phenyl or phenyl-C$_{1-4}$-alkyl group which is unsubstituted or substituted by 1 or 2 substituents selected from the group consisting of halogen, methyl, and methoxycarbonyl; or a 5- or 6-membered heterocyclic group containing 1 to 4 hetero-atoms selected from the group consisting of oxygen, sulfur, and nitrogen; or its salt.

6. A method of preventing or treating fungus infection diseases which comprises administering an effective amount of a compound of the formula (I) in claim 1 together with a carrier, excipient or diluent to human beings, livestock, or poultry.

7. An antifungal composition comprising an antifungal effective amount of a compound or a salt thereof as claimed in claim 1, and a carrier, excipient, or diluent.

8. An antifungal composition comprising an antifungal effective amount of a compound or a salt thereof as claimed in claim 2, and a carrier, excipient, or diluent.

9. An antifungal composition comprising an antifungal effective amount of a compound or a salt thereof as claimed in claim 3, and a carrier, excipient, or diluent.

10. An antifungal composition comprising an antifungal effective amount of a compound or a salt thereof as claimed in claim 4, and a carrier, excipient, or diluent.

11. A compound of claim 1 which is [(2RS,3RS)-3-(2,4-difluorophenyl)-3-hydroxy-4-(1H-1,2,4-triazol-1-yl)-2-butyl] N,N-diethyldithiocarbamate or a pharmaceutically acceptable salt thereof.

12. A compound of claim 1 which is [(2R,3R)-3-(2,4-difluorophenyl)-3-hydroxy-4-(1H-1,2,4-triazol-1-yl)-2-butyl]N,N-diethyldithiocarbamate.

13. A compound of claim 5 which is [(2R,3R)-3-(2,4-difluorophenyl)-3-hydroxy-4-(1H-1,2,4-triazol-1-yl)-2-butyl]N-methyl-N-(3-methylphenyl)dithiocarbamate.

14. A compound of claim 1 which is [(2R,3R)-3-(2,4-difluorophenyl)-3-hydroxy-4-(1H-1,2,4-triazol-1-yl)-2butyl]dibutyldithiocarbamate.

15. A compound of claim 1 which is [(2R,3R)-3-(2,4-difluorophenyl)-3-hydroxy-4-(1H-1,2,4-triazol-1-yl)-2-butyl]N-phenyldithiocarbamate.

16. A compound which is [(2R,3R)-3-(2,4-difluorophenyl)-3-hydroxy-4-(1H-1,2,4-triazol-1-yl)-2-butyl]N-(2methoxycarbonylphenyl)dithiocarbamate.

17. A compound which is [(2R,3R)-3-(2,4-difluorophenyl)-3-hydroxy-4-(1H-1,2,4-triazol-1-yl)-2-butyl]N(2,3-difluorophenyl)dithiocarbamate.

18. A compound which is [(2R,3R)-3-(2,4-difluorophenyl)-3-hydroxy-4-(1H-1,2,4-triazol-1-yl)-2-butyl]N-(4-trifluorophenyl)dithiocarbamate.

19. A compound of claim 1 which is [(2R,3R)-3-(2,4-difluorophenyl)-3-hydroxy-4-(1H-1,2,4-triazol-1-yl)-2-butyl]N-(2-phenylethyl)dithiocarbamate.

20. A compound which is [(2R,3R)-3-(2,4-difluorophenyl)-3-hydroxy-4-(1H-1,2,4-triazol-1-yl)-2-butyl]N-(2,4-dichlorophenyl)dithiocarbamate.

21. A compound of claim 1 which is [(2R,3R)-3-(2,4-difluorophenyl)-3-hydroxy-4-(1H-1,2,4-triazol-1-yl)-2-butyl]N,N-dimethyldithiocarbamate.

* * * * *